US009808497B2

(12) United States Patent
Goel

(10) Patent No.: US 9,808,497 B2
(45) Date of Patent: Nov. 7, 2017

(54) FORMULATIONS OF CONCENTRATED PRUNES AND PREBIOTICS AS LAXATIVES AND DIETARY SUPPLEMENTS

(71) Applicant: Jiva Pharma, Inc., Ann Arbor, MI (US)

(72) Inventor: Om P Goel, Ann Arbor, MI (US)

(73) Assignee: Jiva Pharma, Inc., Ann Arbor, MI (US)

( * ) Notice: Subject to any disclaimer, the term of this patent is extended or adjusted under 35 U.S.C. 154(b) by 0 days.

(21) Appl. No.: 14/354,023

(22) PCT Filed: Nov. 2, 2012

(86) PCT No.: PCT/US2012/063414
§ 371 (c)(1),
(2) Date: Apr. 24, 2014

(87) PCT Pub. No.: WO2013/067424
PCT Pub. Date: May 10, 2013

(65) Prior Publication Data
US 2014/0308374 A1    Oct. 16, 2014

Related U.S. Application Data

(60) Provisional application No. 61/556,252, filed on Nov. 6, 2011, provisional application No. 61/597,799, filed on Feb. 12, 2012, provisional application No. 61/636,067, filed on Apr. 20, 2012, provisional application No. 61/677,662, filed on Jul. 31, 2012.

(51) Int. Cl.
| | |
|---|---|
| A01N 65/00 | (2009.01) |
| A61K 36/736 | (2006.01) |
| A61K 36/28 | (2006.01) |
| A61K 31/702 | (2006.01) |
| A23L 2/02 | (2006.01) |
| A23L 2/52 | (2006.01) |
| A23L 2/60 | (2006.01) |
| A61K 45/06 | (2006.01) |
| A61K 31/122 | (2006.01) |
| A61K 36/48 | (2006.01) |
| A61K 47/36 | (2006.01) |
| A23L 29/30 | (2016.01) |
| A23L 33/00 | (2016.01) |
| A23L 33/105 | (2016.01) |
| A23L 33/15 | (2016.01) |
| A23L 33/16 | (2016.01) |
| A23L 33/175 | (2016.01) |
| A23L 33/21 | (2016.01) |
| A61K 47/10 | (2017.01) |

(52) U.S. Cl.
CPC .............. *A61K 36/736* (2013.01); *A23L 2/02* (2013.01); *A23L 2/52* (2013.01); *A23L 2/60* (2013.01); *A23L 29/37* (2016.08); *A23L 33/105* (2016.08); *A23L 33/15* (2016.08); *A23L 33/16* (2016.08); *A23L 33/175* (2016.08); *A23L 33/21* (2016.08); *A23L 33/40* (2016.08); *A61K 31/122* (2013.01); *A61K 31/702* (2013.01); *A61K 36/28* (2013.01); *A61K 36/48* (2013.01); *A61K 45/06* (2013.01); *A61K 47/36* (2013.01); *A61K 47/10* (2013.01)

(58) Field of Classification Search
CPC ....................................................... A61K 36/00
USPC ........................................................ 424/725
See application file for complete search history.

(56) References Cited

U.S. PATENT DOCUMENTS

| | | | |
|---|---|---|---|
| 3,440,183 A * | 4/1969 | Stephens, Jr. | A23L 1/22671 512/11 |
| 6,623,779 B1 * | 9/2003 | Huxsoll | A23L 1/0532 426/138 |
| 7,977,319 B1 | 7/2011 | Levine | |
| 2005/0053676 A1 | 3/2005 | Schata et al. | |
| 2008/0044493 A1 | 2/2008 | Sato et al. | |
| 2011/0123651 A1 * | 5/2011 | Mower | A23L 1/3002 424/732 |
| 2011/0135758 A1 | 6/2011 | Thomas | |

FOREIGN PATENT DOCUMENTS

| | | |
|---|---|---|
| EP | 2014181 A2 | 1/2009 |
| JP | 1989-197440 A | 8/1989 |
| TW | 200840490 | * 10/2008 |
| WO | 00/48585 | 8/2000 |

OTHER PUBLICATIONS

"Various sources of citric acid", 19 pages, 2012.*
"Chatelaine", 5 pages, 2012.*
"9 Fruits You Should Treat with Extreme Caution", 10 pages, 2014.*
M. Pettigrew, Quality in Health Care, 2001, vol. 10, pp. 268-273.
Sennoside Tablets, 12 mg, "Fuso", 2007, pp. 1-2.
(Continued)

*Primary Examiner* — Michael Meller
(74) *Attorney, Agent, or Firm* — Technology Law PLLC; Karen L Kimble

(57) ABSTRACT

The present invention describes a formulation comprising a prune and/or plum concentrate, and one or more water-soluble, non-digestible, prebiotic oligosaccharides. Optionally, one or more low calorie sweeteners, an antioxidant, calcium sennosides, or sennosides extract, PEG-3350, licorice, cocoa, coffee, tea flavors; fruit flavorings and spice flavorings, gelatin, agar-agar, carrageenan, pectin or cocoa powder are added. Other ingredients may be present as dietary supplements such as water-soluble vitamins, lipid-soluble vitamins; amino acids, maltodextrin, resveratrol, caffeine, mineral supplements, or natural sleep aids for use as a laxative, A variety of formulations are possible, such as premix, a laxative+energy power drink or power bar, or as a prebiotic supplement in probiotic yogurts, or in the form of gummies, chocolates, candies, and desserts such as red beans Japanese desserts. These present formulations are improved for taste, fast acting, portable and palatable laxatives, and as dietary supplements.

1 Claim, No Drawings

(56) References Cited

OTHER PUBLICATIONS

Valley View Packing, 'Prune Juice Concentrate Specifications: 70 Brix', [online], Apr. 19, 2011; URL:http://www.sacramentopacking.com/uploads/04-19-2011_Valley_View_Prune_Juice_Concentrate_Specifications_70_Brix.pdf]; p. 1-2.

Brand's, 'Brand'S InnerShine Prune Essence' [online], Nov. 14, 2007; URL: http://web-beta.archive.org/web/20071114010954/http://www.brandsworld.com.my/cms.ww/main.aspx?sid=336]; p. 1-2.

Anonymous; "Fig and Plum Concentrate"; Oct. 2007; XP002742108.

Anonymous; "Plum and Apple Cereal Bar"; Dec. 2010; XP002742109.

Anonymous; "Prune Essence"; Oct. 2010; XP002742110.

U Sairanen et al.; European J. of Clinical Nutrition; vol. 61 (12); Feb. 14, 200; pp. 1423-1428; XP055201612.

P. Ramnani et al.; British J. of Nutrition, vol. 104 (02); Mar. 1, 2010; pp. 233-240; XP055201660.

Dikeman C. L. et al.; J. of Agricultural and Food Chem.; ACS (US); vol. 52 (4); Jan. 1, 2004; pp. 853-859; XP009056020.

Valley View Packing; "Specification No. 110-12-7R Prune Juice Concentrate Specifications 70RIX"; Apr. 19, 2011; XP055149552.

\* cited by examiner

US 9,808,497 B2

FORMULATIONS OF CONCENTRATED PRUNES AND PREBIOTICS AS LAXATIVES AND DIETARY SUPPLEMENTS

CROSS REFERENCE TO RELATED APPLICATIONS

This application is a national phase application from International Application PCT/US2012/063414, filed Nov. 2, 2012, and is claiming benefit of four U.S. provisional applications having U.S. Ser. No. 61/556,252, filed on Nov. 6, 2011, U.S. Ser. No. 61/597,799, filed on Feb. 12, 2012, U.S. Ser. No. 61/636,067, filed on Apr. 20, 2012, and U.S. Ser. No. 61/677,662, filed on Jul. 31, 2012. The disclosure of each application is incorporated by reference to the extent it is not in conflict with this application.

FIELD OF THE INVENTION

The present invention concerns the preparation and use of formulations made from plums or prunes or both, together with prebiotics and optional other ingredients, as effective laxatives, and may contain other dietary supplements. These formulations may be in a variety of forms for consumption.

BACKGROUND OF THE INVENTION

Regular, daily bowel movements are helpful, even essential, in maintaining a good appetite, an overall sense of well-being, good energy levels, and a positive attitude. They also can aid in prevention of various gastrological conditions developing. However, constipation (meaning fewer than three passing of stools per week or of hard and dry stools, which cause a bloated feeling and possible painful hemorrhoids) is a common health concern in the general population, especially the elderly. Left untreated, constipation may induce abdominal pains, weight gain, and psychological distress. According to the National Institute of Diabetes and Kidney Diseases (NIDDK, 2010), 63 million US adults suffer from chronic constipation. Children under the age of 15 are the second most afflicted group. Thus, presently there is a huge market need for regularity-directed supplements and safe, everyday use, over--the-counter (OTC) medications. (A. Elizabeth Sloan; *Neutraceuticals World*; "Sloan Trends," May 2012, pp. 16-17).

Over the centuries, numerous, palliative, naturally occurring or man-made synthetic chemical remedies have been available to induce bowel movement or to loosen the stool and treat constipation. Many of these agents are available as over-the-counter (OTC) remedies to consumers. Like most remedies, however, there is wide variation in their effectiveness and individual preferences for each class of laxatives. For example, popular natural fibers, and bulk-forming agents such as psyllium seed husks [sold as Metamucil® (trademark of Procter & Gamble Company), Benefiber® (trademark of Novartis AG)], guar gum, bran and others, exert their effect by bulking up the stool by retaining more water; therefore these agents must be consumed with plenty of water. However, these agents are not immediately effective, can require a person to take up to 3 doses per day, and are tiresome to consume in large amounts of water. Also, in some individuals, these agents simply do not work. Another fiber product is FiberChoice® (trademark of GlaxoSmithKline), a chewable tablet form, containing a moderate amount (4 g) of a vegetable derived fiber, inulin.

U.S. Pat. No. 7,977,319 claims an ultra-thigh fiber supplement made with guar, oat, psyllium, locust bean gum, pectin, and vitamins for weight loss and better cardiovascular health.

The chemical stimulant laxatives, which work on the intestinal mucosa, are based on the active chemical structural motifs of anthraquinone [e.g., cascara, buckthorn, aloe vera, and senna extract sold as Senokot® (trademark of Purdue Frederick Company)], or triphenylmethane (e.g., bisacodyl) or a stool softener, such as sodium docusate, a surfactant, sold as Dulcolax® (trademark of Boehringer Ingelheim). These chemical stimulant laxatives are used when gentler, natural laxatives have not worked over several days, such as can happen during travel in different time zones affecting circadian rhythms or consuming foods that are not customary for that person and possibly more difficult to digest, and next day relief is needed. However, these agents are not recommended for chronic use and should be used with care or as directed by a physician because they can have serious side-effects. See, for example, an article by Joo J., et al., "Alterations in colonic anatomy induced by chronic stimulant laxatives: the cathartic colon revisited", *J. Clin. Gastroenterology* 26(4), 283-6 (1998).

Another popular OTC laxative is based on the use of the chemical polyethylene glycol, or PEG-3350, sold as SoftLax, MiraLAX® (trademark of MSD Consumer Care, Inc.) or GlycoLax® (trademark of Kremers Urban Development Co.). These products work as an osmotic laxative, by drawing water into the colon thereby promoting bowel movement. This laxative will usually cause a bowel movement in one to three days, and may be taken for a short term, up to 7 days, for relief of chronic constipation.

One home remedy that is long recognized for its gentle, reliable, fast acting laxative effect is prunes, which are hot air dried plums. Prunes are remarkable in that they will not spoil or rot even for years stored at room temperature in open air, due to their having a very high antioxidative potential. Daily consumption at breakfast of 6-7 oz, of prune juice (extract), available in most US grocery stores, is reliably effective in promoting same day bowel movement and has been shown safe even when used for decades. There are no known side-effects.

Alternatively, one may consume 8-10 dry prunes or soft moist pitted prunes with breakfast, an unwelcome chewing exercise as they are often tough to chew and have a gummy mouth feel. These are available in portable pouches in various sizes.

The mechanism of action of the laxative effect of prunes is not known. Prunes contain the sugar alcohol sorbitol, a non-stimulant laxative, and the natural laxative dihydrophenyl isatin (see Vivek Kumar, et al., *Clinical Geriatrics*, April 2007, pp. 37-42), and about 6% or 0.06 g of dietary fiber per g of prunes. Sorbitol, a hyperosmotic agent, causes the intestines to flood with water, softening the stools and promoting bowl movement.

Various improved formulations of prunes have been proposed. US Application 20030012862, published Jan. 16, 2003, proposes encapsulating prune powder from pulverized prunes. However, the proposed dose of 750 mg of prune powder in capsules falls far short of any known effective dose.

Another highly advertised product is Prunelax® (trademark of Laboratorios Garden House Farmaceutica S.A.) administered as a tablet (dose 2-3, tablets at bedtime) or capsule (dose 4-6 capsules at bedtime). Each tablet contains a small amount (125 mg) of dried prune extract, 960 mg of powdered senna leaves and 180 mg of powdered senna pods derived from the leaves and pods of the senna plant (*S. Alexandrina* or *S. Angustifolia*). The active ingredient of senna is the same anthraquinone derivatives as mentioned above as their dimeric glycosides A and B, in the chemical stimulant category as noted above (Merck Index, XIII Edition; 8528, 8529). Despite the name, the prune content of these tablets or capsules is almost negligible to have a significant contributory laxative effect.

A free flowing granular prune powder, containing a small amount of calcium stearate, is available from Mayan Sun Co. in Washington State. The powder is prepared by further drying of prunes and then pulverizing into a powder. It is ~80% by weight of prunes. Adding and stirring 47.5 g of this powder (equivalent ~10 prunes) in 175 mL of warm water makes a very thick suspension with a bitter taste. It is unsuitable for the desired application.

U.S. Pat. No. 5,573,232 claims a prune formulation having an ingestible syrup for softening the stool and improving regularity of elimination by mixing 1-10% by volume of psyllium powder in prune concentrate (actually a prune puree from whole prunes) at the point of ingestion. It forms into a very thick syrup and is unsuitable and unappetizing for the purpose.

US Patent Application 20110135758 claims a process for producing a laxative containing a mixture of prune juice, magnesium, magnesium hydroxide and purified water. Magnesium hydroxide has laxative properties (see Merck Index). However, mixing metallic magnesium with prune juice is not understood as to its purpose.

The use of dietary supplements is currently a popular multibillion dollar US market for products such as quick energy drinks with nearly 50 brands available, e.g. 5-hour Energy® (trademark of Living Essentials, LLC), which combines in water, megadoses of water soluble B-vitamins, amino acids, and caffeine in a ~2 oz bottle. These products do not provide a laxative that can taste pleasant with these ingredients.

Clearly, a safe, reliable, pleasant tasting formulation for use as a laxative or as a regularity-directed supplement in adults and teens that can be used repeatedly over long periods of time is needed.

BRIEF SUMMARY OF THE INVENTION

The present invention comprises a formulation of concentrated prunes with prebiotics, i.e., non-digestible, naturally occurring oligosaccharides, which is a subset of starch, which promote the growth of beneficial bacteria in the colon for greater efficacy as a laxative, or as a dietary supplement to relieve occasional or habitual constipation, promote regularity, and colon health. The present formulation has a pleasant taste and can be used over long periods of time. The present formulation is convenient for traveling. It may be supplied in 1-2 oz. tear-open plastic or biodegradable packets, (e.g., as used for single servings of mustard, mayonnaise or ketchup), or as single-use, filled wide-straws, or in peel-open small containers (e.g., used for breakfast jellies, jams, peanut butter, or honey, to spread on a toast, muffins or rolls), in puddings or other desserts; or as quick energy, cereal-containing power bars or breakfast bars (as sold in most US grocery stores by Kellogg® or General Mills® or others); or in a single serving of yogurt (as sold by Dannon® or Yoplait® and others); or in frozen yogurt; smoothies; ice slushes; and as fruit roll-ups. The concentrated product is reconstituted by stirring in warm water, tea or coffee and can be stirred into soda or juice. Alternatively, it may be supplied in small containers such as from about 2 to about 8 oz. bottles or individual drink cartons, or in larger jars as an at-home remedy. The present formulation is enjoyable to drink and at least as effective as 7-8 oz. of prune juice that is available in many grocery stores.

Alternatively, the present formulation may be combined with gelatin, heated and then molded into 3-10 g size gummies in a convenient multi-unit packaging for easy to enjoy, on-the-move use. Alternatively, small pieces or chips of gummies may be added to a morning bowl of one's favorite cereal, in trail-mixes; fruit chews, and as sour gummies. For vegan consumers, gelatin may be replaced with vegetable gelling agents such as agar-agar, carrageenan, pectin and others. The vegetable gelling agents are also water soluble prebiotic starches that are known to exert a laxative effect (Wikipedia). The latter may be delivered in popular Japanese (anmitsu, mizuyokan), Philippines, and Vietnamese desserts.

Alternatively, the present formulation may be combined with cocoa powder, and offered as sweet or dark chocolates, caramels, fudge, toffee, mints, as a liquid-center filling in chocolate truffles, or in liquid-center gums in a manner such as Bubllicious Bursts™ (trademark of Cadbury Adams, a division of Kraft Foods), or Freshen-Up™ (trademark of Kraft Foods Global Brands LLC).

The present laxative formulation comprises:
1) a prune or plum concentrate or a mixture thereof wherein the concentrate is from ≥70 Brix (° Bx); and
2) one or more water-soluble, non-digestible, prebiotic oligosaccharides.

Alternatively, a laxative formulation of this invention comprises:
1) a prune or plum concentrate or a mixture thereof wherein the concentrate is about ≥70 Brix(° Bx); and
2) one or more water-soluble, non-digestible, prebiotics, such as inulins, oligogalactosaccharides and/or lactosucrose; and
3) optionally adding calcium sennosides, with an assay result about 60% by USP, or about 3 to about 8% water-ethanol sennosides extract in the form of a powder from the pods and/or leaves of the senna plant (*S. Alexandrina* or *S. Angustifolia* or *S. Cassia*); or
4) optionally adding polyethylene glycol-3350 (PEG-3350) powder, e.g., supplied by The Dow Chemical Company as Carbowax™.

One or more additional ingredients may be present in these formulations, including, but not limited to one or more low calorie sweeteners, sorbitol, xylitol, psyllium husk fiber, guar gum fiber, fruit flavorings, pharmaceutical grade silica, and calcium stearate and the ingredients in step c) below.

The formulation is prepared by the following steps comprising:
a) Mixing a prune or plum concentrate, wherein either concentrate is 100% alone or as a mixture of the two; and
b) Adding water-soluble, non-digestible, prebiotic oligosaccharides, to the concentrate in part (a) and then adding water as needed to form a stirable mixture; and
c) Optionally adding with stirring to the mixture in part (b), one or more of: a low calorie sweetener or mixtures thereof; a food approved antioxidant; calcium sennosides, or sennosides extract; PEG-3350; a natural sleep aid; water-soluble vitamins; emulsified lipid-soluble vitamins; mineral supplements; caffeine; amino acids; maltodextrin; resveratrol; gelatin, or a vegetable gelling agent (such as agar-agar, carrageenan, or pectin); cocoa powder; and licorice, fruit, spice or other flavorings; and d) Heating and stirring the mixture in part (b) or part (c) from about 40 to about 90° C. to provide a homogeneous product; and e) Optionally filtering the product in part (d) through an in-line viscous fluid filter (such as one from Russell Finex Co., Pineville, N.C.), or a medium porosity ceramic filter, or a fine mesh stainless steel screen, to remove insoluble particulates; and f) Metering the mixture from part (d) or (e) into the desired product: (i) in a container (such as a single serving container of any type); (ii) in a yogurt; (iii) forming it into a power bar, energy bar or breakfast bar; (iv) mixing with a gelatin, agar-agar, carrageenan, or pectin mixture and cooling into molds to form gummies or as fruit roll-ups; (v) forming desserts (such as Japanese (anmitsu, mizuyokan), Philippines, and Vietnamese desserts); (vi) forming candies (such as a liquid-center filling in chocolate truffles, or in liquid-center gums); or (vii) forming chocolates (such as sweet or dark chocolates or fudge, mints, caramels, toffee, truffles, and bonbons); or g) spray drying the further water diluted mixture having maltodextrin with hot air at about 120 to about 160° C. to yield the formulation as a powder, which may be blended with pharmaceutical grade silica and/or calcium stearate for maintaining desired powder flow properties.

The concentrate can be either prune or plum concentrate as a 100% by weight mixture or a mixture of both prune concentrate and plum concentrate in a ratio of from about 1:99 to about 99:1% by weight. The concentrate has sweetness of ≥70 Brix (° Bx); however, if due to evaporation conditions of the puree the concentration of >70 Brix is not attained; the puree concentrate of at least about 43 to about 70 Brix (° Bx) can be used. Such concentrate contains water but some additional water may be added if necessary to have a more fluid mixture.

A second component in the formulation is water-soluble, non-digestible, prebiotic oligosaccharides (which are a subset of starches) such as inulins, galactooligosaccharides (GOS), lactosucrose, or a mixture thereof. The ratio of prune or plum concentrate to water-soluble, non-digestible, prebiotic oligosaccharides is from about 90% of concentrate by weight to about 10% of oligosaccharides by weight, preferably from about 60% of concentrate by weight to about 40% of oligosaccharides by weight, inclusive of the range of about 90 to about 60% by weight of the concentrate by weight to about 10 to about 40% by weight of the oligosaccharides.

The present formulation is administered as a laxative or dietary supplement formulation to an animal or human in need of such treatment in the amount of from about 15 to about 200 g/day, preferably from about 25 to about 150 g/day.

This application claims priority from U.S. Provisional Application 61/556,252, filed on Nov. 6, 2011, U.S. Provisional Application 61/597,799, filed on Feb. 12, 2012, U.S. Provisional Application 61/636,067, filed on Apr. 20, 2012, and U.S. Provisional Application 61/677,662, filed on Jul. 31, 2012, all of which are hereby incorporated by reference.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

The following terms as used in this application are to be defined as stated below and for these terms, the singular includes the plural.

° Bx means Brix, which is the sugar content of an aqueous solution. One degree Brix is 1 g of sucrose in 100 g of solution and represents the strength of the solution as percentage by weight (% w/w) (strictly speaking, by mass). If the solution contains dissolved solids other than pure sucrose, then the ° Bx only approximates the dissolved solid content.

FOS means fructose oligosaccharides.

GH means glycoside hydrolases.

GOS means galactooligosaccharides.

GRAS means Generally Recognized As Safe under §§201(s) and 409 of the Federal Food, Drug, and Cosmetic Act (US FDA), that is any substance that is intentionally added to food is considered a food additive, that is subject to premarket review and approval by US FDA, unless the substance is generally recognized, among qualified experts, as having been adequately shown to be safe under the conditions of its intended use, or unless the use of the substance is otherwise excluded from the definition of a food additive.

OTC means over-the-counter.

PEG-3350 means polyethylene glycol of an average molecular weight of 3350.

Resveratrol means 3,5,4'-trihydroxy-trans-stilbene or 5-(p-hydroxystyryl)resorcinol or 5-(4-hydroxystyryl)benzene-1,3-diol.

Sennoside extract means a standardized water/ethanol extract of senna pods and leaves, isolated as a powder by evaporation of the extract.

Discussion

Because of the deficiencies in the prior known laxative or regularity-directed dietary supplement formulations, alternative, improved, faster acting, portable, pleasant tasting, palatable formulations are needed. Such a formulation better insures compliance for those who need it, especially hospital patients, elderly persons, teenage children, or even toddlers. These ingredients are natural compounds with the exception of the artificial sweeteners and PEG-3350. The present formulations are made from plums or prunes or both, and water-soluble, non-digestible prebiotics that provide an effective, faster acting, portable laxative than prune juice. Such an improved formulation is provided by this invention.

The first ingredient of this present formulation is derived from plums. These plums can be organically grown if desired. Fresh California grown French plums or hot air dried plums (prunes) are converted to their purees through steaming for softening, pitting, and then pulping. The purees have numerous applications in baking as a substitute for butter, in dairy products, confectionary, sauces and other applications. The suspended insolubles in the mixture are removed from the water diluted purees by passing through medium and fine mesh screens, and then blended in a high speed homogenizer. The resulting water extracts are concentrated in a still or on a heated drum dryer. The sugar content of the plum or prune concentrates is >43 Brix and is further enhanced by concentration, further evaporation, to ≥70 Brix (° Bx), from that of initial 33 Brix (° Bx) in the purees. The concentrate preferably has sweetness of ≥70 Brix (° Bx); however, if due to evaporation conditions of the puree the concentration of ≥70 Brix is not attained; the puree concentrate of at least about 43 to about 70 Brix (° Bx) can be used. (Stapleton-Spence Packing Company, San Jose, Calif.).

The concentrate can be either prune or plum concentrate as a 100% by weight mixture or a mixture of both prune concentrate and plum concentrate in a ratio of from about 1:99 to about 99:1% by weight. The preferred concentrate has sweetness of ≥70 Brix (° Bx). Such concentrate contains water but some additional water may be added if necessary for better stirring.

Prune concentrate is ¼th the volume of prune puree. The prune juice sold in US grocery stores has 18.5% by weight prune solids vs. 70% by weight in prune concentrate or plum concentrate, which makes the concentrates better suited to develop into the present formulations having greater laxative potency. The concentrates have the consistency of molasses. The plum concentrate is pleasant tasting; whereas the prune concentrate has a slightly bitter taste.

The second ingredient in the present formulation is one or more water-soluble, non-digestible, prebiotic oligosaccharides (these oligosaccharides are a subset of starches). They pass through intact in the upper gastrointestinal tract, and thus have reduced caloric value. A prebiotic beneficially affects the host by selectively stimulating the growth and activity of one or a limited number of bacteria (such as bifidobacteria and lactobacilli) in the colon, thus improving the host's digestive health. Such complex carbohydrates act as food substrates for the beneficial bacterial growth in the colon, and that lactic acid and acetic acid produced by these bacteria promote intestinal peristaltic movement and defecation. These oligosaccharides include fructooligosaccharides, lactosucrose, and galactooloigosaccharides (GOS).

In contrast, a probiotic is a live microbial food supplement, such as found in yogurts, which beneficially affects the host by improving its intestinal microbial balance.

Suitable water-soluble, non-digestible, prebiotic oligosaccharides are: inulins, galactooligosaccharides (GOS), and lactosucrose, or a mixture of these. Inulin is a natural storage carbohydrate in the fructose oligosaccharides class (FOS) (10-60 fructose units, capped by a glucose unit at the end) and has various molecular weights (MW). Several commercial grades of inulin (≤10 fructose units) are available that have a neutral, or sweet clean flavor. (Some examples are Oliggo-Fiber® brands, or L-85® or L-90® (as syrups) marketed in the U.S. by the Cargill Health and Nutrition, Minneapolis, and Gillco Ingredients, Maywood, Calif.). The inulin used in this invention can be a mixture of these various MW inulins that are mostly non-digestible. Inulin is found in chicory roots, artichokes, onions, wheat, barley and bananas and is ⅒ as sweet as sugar. It is a free flowing, heat stable, white powder. It is the active ingredient in chicory roots, believed to have laxative effects. Various in vitro and in vivo studies have shown that a diet supplemented with B(2-1) inulin/FOS provides an effective means to promote growth of bifidobacteria and lactobacilli in the colon, while selectively reducing the growth of pathogenic microorganisms and potentially treating intestinal dysfunctions [Bryan C. Tungland, Duncan Crow, "Inulin: A Comprehensive Scientific Review", *Wholistic Consultant,* 2000; Thomas Barclay, et al., "Inulin—a versatile polysaccharide with multiple pharmaceutical and food chemical uses", *J. Excipients and Food Chem.* 1(3), 27-50 (2010); Kathy R. Niness, "Inulin and Oligofructose: What Are They?" *J. Nutr.*, Jul. 1, 1999, 129(7), 1402S-1406s].

The galactose oligosaccharides (GOS) are di- to hexa-saccharides which are formed when lactose is treated with the enzyme glycoside hydrolases (GH). The commercially available GOS preparations contain 14-25% unreacted lactose. (Duarte P. M. Torres, et al., "Galacto-oligosaccharides; Production, Properties, Applications and Significance as Prebiotics" *Comprehensive Reviews in Food Science and Safety,* 9(5), 438-454, September 2010). The presence of significant amounts of lactose in commercial preparations of GOS limits its use in formulations for consumers who are lactose intolerant. The principal component of 4'-galactosyl lactose is found in human milk The commercially available GOS syrups (mainly β 1-4 linkages) are used as food ingredients, and in infant formulae, for example in Similac™ (trademark of Abbott Laboratories), and Enfamil™ (trademark of Mead Johnson & Co.) in 2-5 g/day in milk, baby cereals and other infant food uses. They have a pleasant sweet clean taste, are ~55 to 60% sugars, and contain 14-25% lactose. These GOS are supplied by: Friesland-Campina Domo, as Vivinal® GOS; the Yokult Pharmaceutical Co., as Oligomate 55N: and Clasado company's Bimuno.

A powder form is produced by spray-drying with maltodextrin. For example, a stirred solution of all desired ingredients is preheated to about 50 to about 90° C., filtered, then pumped as a thin spray through a nozzle into the spray dryer chamber through which is passed hot dry air at from about 120 to about 150° C. The air used is a dry, sterile air. The powder is collected at the bottom of the spray dryer and may be used in the prunes containing formulations.

The influence of GOS use has been shown to increase the frequency of defecation [Deguchi, Y., et al., "Effects of beta 1-4 galactooligosaccharides administration on defecation of healthy volunteers with a tendency to constipation", *Jap. J of Nutr.* 55(1), 13-22 (1997); and Teuri U., et al. "Galacto-oligosaccharides relieve constipation in elderly people", *Ann. Nutr. Metabolism* 42, 319-327 (1998). Yoriki Deguchi, et al., "Influence of Galacto-oligosaccharides on Bowel Habit in Healthy Young Volunteers with Constipation Tendency", *Journal of Japanese Council for Advanced Food Ingredients Research.* 2003; 6(2):55]. US patent application 20110003768 claims a mixture of oligo-fructosides and oligo-galactosides for synergistically promoting the growth of lactobacilli. These formulations do not include prunes or plums.

Lactosucrose, which is a tri-saccharide, comprises galactose, glucose and fructose and occurs naturally during yogurt making in which sucrose and lactose present in milk are fermented by *lactobacillus vulgalicas.* (e.g., Suyama, K., et al., *Animal Science Journal Lecture summary,* 88, 276 (1994).) Lactosucrose is a prebiotic and is approved by the Japanese Ministry of Health and Welfare as a food for special dietetic use due to its beneficial effects in proliferating bifidobacteria and improving bowel movement.

When a mixture of these oligosaccharides is used, for example the ratio of inulins to GOS and/or lactosucrose is from about 1:99 to about 99:1% by weight of inulins. For patients who may experience adverse effects of exposure to lactose containing products, only inulins may be used in the formulations.

The ratio of prune or plum concentrate to water-soluble, non-digestible, prebiotic oligosaccharides is from about 90% of concentrate by weight to about 10% of oligosaccharides by weight, preferably from about 60% of concentrate by weight to about 40% of oligosaccharides by weight. Various ranges between these stated values can also be used, e.g., 70% of concentrate by weight to 30% of oligosaccharides by weight.

Various additional ingredients can be included, as desired, in the present formulation. For example, such ingredients are: low calorie sweeteners; a food approved antioxidant; calcium sennosides or sennosides extract; PEG-3350; natural sleep aid; water-soluble vitamins; emulsified lipid-soluble vitamins; mineral supplements; resveratrol, gelatin, agar-agar, carrageenan, pectin; cocoa powder; caffeine; amino acids; maltodextrin; and licorice, fruit, spice or other flavorings.

One such ingredient is one or more low calorie sweeteners such as xylitol, sorbitol, or an artificial sweetener or mixture thereof. Some examples of such sweeteners are: aspartame (e.g., Equal®, trademark of Merisant Company) and/or sucralose (e.g., Splenda®, trademark of McNeil Nutritionals, LLC, which is a sucralose-based artificial sweetener derived from sugar, blended with maltodextrin) and/or stevia (e.g., Truvia®, a trademark of The Coca-Cola Company, which is a low caloric sweetener derived from the stevia plant and blended with erythritol), or 99% pure Rabaudioside A, also derived from *Stevia Rebetudiana* leaves (e.g., Good & Sweet® trademark of Blue California). Xylitol is a low caloric naturally occurring sweetener, used in chewing gums, and is classified as a GRAS substance. Xylitol imparts a pleasant taste to the reconstituted formulated product of this invention in water. Sucralose and aspartame are well-known artificial sweeteners.

The proportion of sweetener, sorbitol and/or xylitol combined in the present formulation is from about 5 to about 35% by weight of the prune or plum concentrate. The amount of Splenda® is from 0.25 to about 1% by weight of the prune or plum concentrate. The amount of aspartame, sucralose, stevia, or sucralose and stevia, or 99% pure Rabaudioside A derived from *Stevia Rebaudiatia* leaves, or Truvia® or Good & Sweet® is from 0.25 to about 2% by weight of the prune or plum concentrate. All of these sweeteners are with or without xylitol. Mixtures of these sweeteners can be used in the present formulation.

Another optional ingredient that can be added to the present formulation is an antioxidant to provide taste improvement or preservation properties as to its taste. Any approved food antioxidant can be used such as ascorbic acid (vitamin C), citric acid, sodium benzoate and others. The proportion of antioxidant used, such as ascorbic acid (vitamin C), citric acid, or sodium benzoate, is from 0.125 to about 2% by weight of the prune or plum concentrate.

Still another optional ingredient that can be added when desired to the present formulation is extracted from a senna plant (*S. Alexandrina* or *S. Angustifolia*, or *Cassia senna*) as its water-soluble, commercially available calcium sennosides, with an assay result about 60% by USP, or about 3 to about 8% water-ethanol sennosides extract in the form of a powder from the pods and/or leaves of the senna plant (*S. Alexandrina* or *S. Angustifolia* or *S. Cassia*); ("sennoside extracts"), in an amount from about 0.05 to about 0.25% by weight of the prune and/or plum concentrate in the formulation. Alternatively, in the above senna formulation, the prune/plum concentrate may be present to the extent of about 0.025 to about 5% by weight of the prebiotic oligosaccharides in order to offer a night time laxative product effective over 6-8 hours.

Also an alternate laxative formulation with or without the prune or plum concentrate comprises: a) one or more water-soluble, non-digestible, prebiotic inulins, oligosaccharides and/or lactosucrose, and b) calcium sennosides or sennosides extract. This nighttime formulation contains the calcium sennosides or sennosides extract from about 0.025 to about 0.25% by weight of the formulation. These optional additional ingredients that can be added to this nighttime formulation are the same as mentioned before; for example, such ingredients are: low calorie sweeteners; a food approved antioxidant; natural sleep aid; water-soluble vitamins; emulsified lipid-soluble vitamins; mineral supplements; nutritional supplement, resveratrol, gelatin, agar-agar, carrageenan, pectin; cocoa powder; caffeine; amino acids; and licorice, fruit, spice or other flavorings.

Also an alternative laxative formulation with or without the prune or plum concentrate comprises: a) one or more water-soluble, non-digestible, prebiotic oligosaccharides and b) polyethylene glycol-3350 or PEG-3350 from about 5% to about 20% by weight of the formulation.

A further optional ingredient that may be added to the present formulation is a natural sleep aid, such as the hormone melatonin, and sleep-inducing herbs such as valerian root, passion flower and/or its extract, hops, chamomile, lemon balm, lavender, and kava kava. This sleep aid is added from about 5 mg to about 50 mg/50 g of the formulation.

Various flavorings can be added to the present formulation for the taste desired, such as licorice, cocoa, coffee, tea flavors; fruit flavorings such as lime, lemon, orange, cherry, strawberry, peach, mixed berry, pomegranate; and spices, such as cinnamon, nutmeg, ginger, chamomile, ginseng, anise, and others.

Currently, there are numerous OTC dietary supplements containing vitamins, minerals, fibers, and/or other desired additives in the form of gelatinous gummies, which formulations are popular among the young and elderly, due to their ease of use, compliance, flavors, and no-need-to-swallow as these may be sucked-on or chewed. Examples of some of these supplements as gummy formulations are: VitaFusion™ (trademark of Northwest Natural Products, Inc.) prenatal and adult vitamin gummies; Citracal™ and Caltrate™ (trademarks of Bayer Consumer Care AG) calcium gummies; FiberAdvance™ and FiberChoice™ (trademarks of GlaxoSmithKline) fiber gummies. Thus, the formulations of this invention may be mixed with hot gelatin, and poured into molds to form gummies. The vegan gummies may be prepared by using vegetable gums such as agar-agar, carrageenan, pectin and others. The vegetable gelling agents are also water soluble prebiotic starches known to exert a laxative effect (Wikipedia). The latter may also be delivered in popular Japanese (anmitsu, mizuyokan), Philippines, and Vietnamese desserts.

Also, the above formulations may be combined and stirred with cocoa powder to form sweet or dark chocolates or caramels, fudge, mints, toffee, and bonbons. The latter may also be offered as liquid center truffles and liquid center gums.

In a further embodiment of the present formulation, ingredients can be added that are for dietary purposes while maintaining the laxative effect. Regular bowel movement is especially important to elderly persons. The present invention addresses this unmet need by combining—in one formulation—ingredients that can work well in nursing homes, hospitals, assisted living, and home care for the elderly. The dietary formulation provides both nutritional needs and laxative in one administration.

Additionally, the significant ingredients of quick energy drinks with the benefits of the present prunes and prebiotics formulations provide a way to assist good health of all persons. This present formulation allows for energy, high fiber, and a laxative in one dose and is pleasant tasting. Such formulation can be a liquid that is reconstituted in another liquid (hot or cold) or formulated into a gummy, chocolates, truffles, liquid-center gums, or power bar (such as an energy bar, a cereal bar or a breakfast bar).

The present formulation can also contain one or more water-soluble B vitamins, and also the lipid-soluble essential vitamins such as A, D, E and K in an emulsified form. Water-soluble B vitamins, present in about 50 g (about 1 dose) of the formulation are thiamine (vitamin B1) from about 2 to about 5 mg, riboflavin (vitamin B2) from about 1.3 to about 1.8 mg, vitamin B6 from about 6 to about 10 mg, vitamin B12 from about 500 to about 1000 mcg, folic acid about 400 mcg, biotin from about 30 to about 100 mcg, niacin from about 16 to about 32 mg, choline from about 400 to about 600 mg and pantothenic acid from about 10 to about 12 mg. Lipid- soluble vitamins, present in about 50 g (about 1 dose) of the formulation, are vitamins A from about 700 to about 3000 mcg, D from about 5 to about 50 mcg, E from about 200 to about 1500 IU, and K from about 90 to about 120 mcg. The level of water-soluble vitamins, and/or lipid-soluble vitamins in a daily dose of the formulation is based on the recommendations of the National Academy of Sciences; *Dietary Reference Intakes for Thiamin, Riboflavin, Niacin, Vitamin B6, Folate, Vitamin B12, Pantothenic Acid, Biotin, and Choline* (1998). National Academy of Sciences. Institute of Medicine. Food and Nutrition Board.

Also mineral supplements can be added in about 50 g of the formulation such as zinc gluconate (from about 15 to about 25 mg) or calcium gluconate, calcium citrate or mineral sources of chromium, iodine, iron, magnesium, and selenium as recommended by the Office of Dietary Supplements, National Institute of Health.

Additionally, resveratrol (a natural product found in red wine and widely studied for its cardioprotective and anti-aging benefits) may be added in the amount of about 20 to about 200 mg in about 50 g of the formulation (Xi Zhao-Wilson, "What dose of Resveratrol should humans take?", *Life Extension Magazine* March 2007).

For energy, caffeine can be included in the formulation in from about 75 to about 350 mg for 50 g of the formulation. Amino acids can be added for dietary purposes if desired. Such amino acids are present in about 50 g of the formulation, and include: taurine or 2-aminoethanesulfonic acid (from about 1000 to about 3000 mg); phenylalanine, or tyrosine or N-acetyl tyrosine (from about 1000 to about 2000 mg); and tryptophan (from about 200 to about 300 mg).

One purpose of the present invention is to enhance the laxative effect of sugars (e.g. sorbitol), and other active ingredients as discussed above in prune and/or plum concentrates by adding oligosaccharides which are in the prebiotic category and which promote the growth of or increase levels of beneficial bifidobacteria and lactobacilli in the large intestine. These oligosaccharides (complex carbohydrates) are claimed to improve digestive health, such as ensuring regular bowel movement (*Chemical & Engineering News*, Oct. 10, 2011, pp. 42-43).

The present formulations may be packaged as unit packets or in bulk. These formulations may be readily reconstituted as pleasant tasting drinks, usually at breakfast, by several means such as: a) stirring in water, tea, coffee, or other warm liquid for easy consumption such as by sipping or by drinking through a straw, or b) adding to a cold soda, tea, coffee or a juice such as a fruit juice, with stirring. Additionally, these formulations may be added to a probiotic yogurt thereby combining the healthful prebiotic benefits of the present formulation with those of probiotics in yogurts, including frozen yogurt, smoothies, ice slushes, or in the form of an easy-to-carry, high fiber content, cereal power bar, energy bar or breakfast bar. These bars and yogurts are made by known methods.

The formulated product packets or containers are readily transportable, a major convenience while traveling. These formulations may be supplied in containers such as ready-to-drink stand-up pouches, bottles or individual drink cartons. These formulations are pleasing to the palate, and portable in a purse or a handbag or a travel bag.

Alternatively, the formulations of this invention may be mixed with hot gelatin and poured into molds to form gummies, including pieces for using on foods such as cereals, trail mixes, fruit chews, or liquid center gum drops. The vegan gummies may be prepared by using vegetable gums such as agar-agar, carrageenan, pectin and others.

Also, the above formulations may be combined and stirred with cocoa powders to form chocolates, caramels, mints, toffee, bonbons, or fudge. These may also be offered as liquid center truffles and liquid center gums. These formulations have the advantage of being solids, which may be consumed over the course of a day, and safer to carry while traveling.

The formulation is administered to a human or an animal in need of a laxative in an amount from about 15 to about 200 g/day, preferably about 25 to about 150 g/day for use as a laxative. This is about 1 to 4 packets, preferably 1 to 2 packets, of the pre-packaged formulation described above. Alternatively, 2-6 gummies/day, or 1-4 chocolates/day may be used.

The invention will be further clarified by a consideration of the following examples, which are intended to be purely exemplary of the invention.

EXAMPLE 1

In a 20 gallon (75 liter) steam-jacketed stirred, stainless steel kettle was added 5 gallons of deionized water, which was heated to 60° C. To this heated solution was slowly added, with rapid stirring, 4.275 lbs (1.94 Kg) of inulin (Giillco Ingredients Co.), and 3.42 lbs. (1.55 Kg) of xylitol (Gillco Ingredients Co.). After stirring vigorously, for 30 minutes, into this mixture was slowly poured 28.5 lbs (12.93 Kg) of pre-warmed prunes or plums concentrates (Stapleton-Spence Co.). The mixture was vigorously stirred and heated to 75° C. for 1 hour, then cooled with stirring to room temperature. It was collected in a 5 gallon plastic pale, and shipped for packing.

EXAMPLE 2

In a 500 gallon (1,900 liter) steam-jacketed stirred stainless steel reactor was added 140 gallons (530 liters) of deionized water, which was heated to 60° C. To this heated solution was slowly added, with rapid stirring, 163.7 lbs. (74.2 Kg) of inulin (Cargill Co.), and 91 lbs. (41.3 Kg) of sorbitol powder (Cargill Co.), and 163.7 lbs. (74.2 Kg) of Oligomate 55 N syrup (Kanematsu Co.), or the GOS syrup (Friesland-Campina Co). After stirring vigorously, for 30 minutes, into this mixture was slowly poured 815.6 lbs (370 Kg) of pre-warmed prunes or plums concentrates (Stapleton-Spence Co.). Natural desired flavoring such as orange extract, 2.4 lbs. (1 Kg) was added. The mixture was vigorously stirred and heated to 75° C. for 1 hour, then hot packed in 1.5 oz. pouches in 50 g dose each.

EXAMPLE 3

The above procedure of Example 1 was repeated using 9.5 lbs (4.3 Kg) of plum concentrate, 0.95 lbs. (0.43 Kg) of xylitol, 1.325 lbs. (0.6 Kg) of inulins, and 2.65 lbs. (1.2 Kg) of Vivinal GOS powder (Friesland.Campino Co.). One-half oz or ~14 gm of natural orange flavor (Jogue Co.) was added with vigorous stirring. After cooling to room temperature, the product was collected in a 5 gallon plastic pale, and shipped for packing.

EXAMPLE 4

In a 20 gallon (75 liter) steam-jacketed, stirred, stainless steel kettle was added 5 gallons of deionized water, which was heated to 70° C. To this heated solution was slowly added, with rapid stirring, 1.324 lbs (0.6 Kg). of inulin (Giillco Ingredients Co.), and 0.95 lbs. (0.43 Kg) of xylitol (Gillco Ingredients Co.), and 19 lbs. (8.64 Kg) of maltodextrin powder (Norben Co.). After stirring vigorously, for 30 minutes, into this mixture was slowly poured 9.5 lbs. (4.3 Kg) of pre-warmed prunes concentrate (Stapleton-Spence Co.). The dilute mixture was fed slowly into a spraydryer (Michigan State University-Dairy, E. Lansing, Mich.) at an inlet temperature of 185° C. and exit temperature of 101° C. There was good powder flow. Collected 15 lbs. (6.8 Kg) of the light brown powder in a plastic lined fiber drum.

EXAMPLE 5

The procedure of Example 2 is repeated using 0.43 Kg of sorbitol, and adding 1.14 Kg of unflavored gelatin with good stirring. The hot product is poured into molds, and the molds cooled to make gummies, each weighing 3-10 g.

EXAMPLE 6

The procedure of Example 2 is repeated using 0.43 Kg sorbitol and 1.14 Kg of cocoa powder. After vigorous stirring, the chocolate containing mixture is poured into molds and cooled to room temperature.

EXAMPLE 7

To a mixture of 0.6 Kg of inulins and 0.43 Kg of Vivinal GOS powder (Friesland Campino Co.) is added 2 L of water, and 1.14 Kg of unflavored gelatin. The mixture is heated and vigorously stirred to 70° C., and calcium sennosides, with an assay result about 60% by USP, or about 3 to about 8% water-ethanol sennosides extract in the form of a powder from the pods and/or leaves of the senna plant (*S. Alexandrina* or *S. Angustifolia* or *S. Cassia*) is added in the amount to produce a 3-5 g gummy to contain 6-20 mg of sennosides. The hot mixture is poured into molds, and cooled to make gummies A statistical sample of gummies is analyzed to determine levels of calcium sennosides. The preparation may include real fruit concentrates such as orange and/or mango or other flavors.

EXAMPLE 8

Example 7 is repeated with cocoa powder to produce sweet or dark chocolates, mints, caramels, toffee, and bonbons. When soft centers of the laxative formulation is desired, these are made by taking small fluted paper cup molds, which are coated with chocolate in the bottom, and all around. A TBS (~10 mL) of the warm liquid formulation is poured in, followed by hot chocolate covering. After cooling, the paper molds are removed.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A laxative formulation consisting essentially of the following components:
   1) a therapeutically effective amount of prune concentrate or plum concentrate or a mixture thereof wherein any suspended insolubles have been removed from the concentrate, and the concentrate is >70 Brix (° Bx);
   2) one or more added water soluble, non-digestible, prebiotic oligosaccharides, selected from inulins having 5-20 fructose units;
   where the ratio of the concentrate to the added oligosaccharides is in a range from about 90%:10% to about 60%:40% by weight:
   3) an added low calorie sweetener selected from sorbitol present in a ratio from about 5% to about 35% by weight of the concentrate; and
   4) an added food approved antioxidant and preservative selected from citric acid present in a ratio of the antioxidant and preservative from 0.125% to about 2% by weight of the concentrate; and
   the formulation is a laxative, having for a single dose 50 g-55 g or 1-2 fluid oz, of the formulation, and which is a pleasant tasting, prebiotic laxative, having the consistency of molasses without any gummy mouth feel.

* * * * *